United States Patent
Jung et al.

(10) Patent No.: US 10,056,221 B2
(45) Date of Patent: Aug. 21, 2018

(54) APPARATUS FOR GENERATING CHARGED PARTICLES

(71) Applicant: ELECTRONICS AND TELECOMMUNICATIONS RESEARCH INSTITUTE, Daejeon (KR)

(72) Inventors: Moon Youn Jung, Daejeon (KR); Jinsun Kim, Daejeon (KR)

(73) Assignee: ELECTRONICS & TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/795,754

(22) Filed: Oct. 27, 2017

(65) Prior Publication Data

US 2018/0139835 A1    May 17, 2018

(30) Foreign Application Priority Data

Nov. 15, 2016 (KR) .................. 10-2016-0152119
Jun. 21, 2017 (KR) .................. 10-2017-0078729

(51) Int. Cl.
| | |
|---|---|
| H01J 27/24 | (2006.01) |
| H05H 1/54 | (2006.01) |
| H01J 27/02 | (2006.01) |
| H01J 37/08 | (2006.01) |
| A61N 5/10 | (2006.01) |

(52) U.S. Cl.
CPC .............. *H01J 27/24* (2013.01); *H01J 27/02* (2013.01); *H01J 37/08* (2013.01); *H05H 1/54* (2013.01); *A61N 2005/1088* (2013.01)

(58) Field of Classification Search
None
See application file for complete search history.

(56) References Cited

U.S. PATENT DOCUMENTS

| | | | | |
|---|---|---|---|---|
| 6,288,390 | B1 * | 9/2001 | Siuzdak | H01J 49/0418 |
| | | | | 250/288 |
| 6,958,480 | B1 * | 10/2005 | Iyer | B01J 20/103 |
| | | | | 250/340 |
| 9,711,319 | B2 * | 7/2017 | Zigler | H01J 27/24 |

(Continued)

FOREIGN PATENT DOCUMENTS

| CN | 104349569 A | 2/2015 |
|---|---|---|
| CN | 104411084 A | 3/2015 |

(Continued)

OTHER PUBLICATIONS

I Prencipe et al., "Development of foam-based layered targets for laser-driven ion beam production", Plasma Physics and Control Fusion, Feb. 17, 2016, pp. 1-8, vol. 58, No. 034019, IOP Publishing Ltd.

*Primary Examiner* — Michael Logie

(57) ABSTRACT

Disclosed is an apparatus for generating charged particles. The apparatus comprises a light source that emits a laser, a target layer that receives the laser to generate charged particles, and a focusing structure that is between the light source and the target source and focuses the laser. The focusing structure comprises solid layers and pore sections alternately and repeatedly disposed along a first direction parallel to a top surface of the target layer. Each of the pore sections comprises a porous layer.

12 Claims, 9 Drawing Sheets

(56) References Cited

U.S. PATENT DOCUMENTS

| | | | |
|---|---|---|---|
| 2002/0090194 A1* | 7/2002 | Tajima | G21K 1/003 385/147 |
| 2003/0183774 A1* | 10/2003 | Tajima | H05H 7/16 250/423 P |
| 2004/0018700 A1* | 1/2004 | Cowan | H01J 27/24 438/513 |
| 2011/0248181 A1* | 10/2011 | Zigler | G21G 1/10 250/423 P |
| 2012/0280138 A1* | 11/2012 | Choi | C23C 14/0005 250/423 P |
| 2013/0138184 A1* | 5/2013 | Jung | A61N 5/1077 607/100 |
| 2013/0153783 A1* | 6/2013 | Zigler | H01J 27/24 250/423 P |
| 2013/0158632 A1 | 6/2013 | Park et al. | |
| 2013/0178689 A1* | 7/2013 | Jung | H01J 27/022 600/1 |
| 2013/0261369 A1 | 10/2013 | Jung et al. | |
| 2013/0289331 A1 | 10/2013 | Jung et al. | |
| 2016/0236011 A1* | 8/2016 | Jung | A61N 5/1077 |
| 2016/0287899 A1 | 10/2016 | Park et al. | |

FOREIGN PATENT DOCUMENTS

| | | |
|---|---|---|
| KR | 10-2013-0070186 A | 6/2013 |
| KR | 10-2015-0129961 A | 11/2015 |

\* cited by examiner

APPARATUS FOR GENERATING CHARGED PARTICLES

CROSS-REFERENCE TO RELATED APPLICATIONS

This U.S. nonprovisional patent application claims priority under 35 U.S.C § 119 of Korean Patent Application Nos. 10-2016-0152119 filed on Nov. 15, 2016 and 10-2017-0078729 filed on Jun. 21, 2017 entire contents of which are hereby incorporated by reference.

BACKGROUND

The present inventive concept relates to an apparatus for generating charged particles, and more particularly, to an apparatus for generating charged particles having improved efficiency in generating charged particles.

Unlike an X-ray or gamma-ray therapy, a therapy using charged particles precisely attacks cancer cells while minimizing damage to normal tissues and thus is paid attention to as a patient-friendly treatment. It has been proposed a method of generating charged particles using a high power pulse laser because existing treatment apparatuses using charged particles require high installation and maintenance costs as well as a large-sized device. Therefore, a therapy apparatus using charged particles has an expectation of reduction in size and cost.

Competitive laser ion accelerators are being developed to generate charged particles whose energy is high enough to remedy tumors located deeply inside the human body. However, recent methods are chiefly being studied to increase only intensity of a laser source so as to produce charged particles of high energy.

SUMMARY

Embodiments of the present inventive concept provide an apparatus for generating charged particles having improved efficiency in generating charged particles.

Embodiments of the present inventive concept provide an apparatus for generating charged particles requiring low cost and increasing energy of charged particles.

The present inventive concept, however, is not limited to the embodiments mentioned described herein.

According to exemplary embodiments of the present inventive concept, an apparatus for generating charged particles may comprise: a light source that emits a laser; a target layer that receives the laser to generate charged particles; and a focusing structure that is between the light source and the target layer and focuses the laser. The focusing structure may comprise solid layers and pore sections alternately and repeatedly disposed along a first direction parallel to a top surface of the target layer. Each of the pore sections may comprise a porous layer.

In some embodiments, the focusing structure may transform into a plasma layer when the laser is irradiated. The plasma layer may comprise free electrons that are distributed to have an electron density reaching a vicinity of a critical electron density of the plasma layer.

In some embodiments, the electron density reaching the vicinity of the critical electron density may be less than and 0.7 times greater than the critical electron density, or may be greater than and 3 times less than the critical electron density.

In some embodiments, each of the pore sections may comprise pores and a boundary layer surrounding the pores.

In some embodiments, the boundary layer may have a uniform distribution in each of the pore sections.

In some embodiments, the boundary layer may have a mesh shape.

In some embodiments, the focusing structure may be obtained from a wing of a swallowtail butterfly.

In some embodiments, the boundary layer may comprise first sub-boundary layers and second sub-boundary layers protruding from a sidewall and an opposing sidewall, respectively, of each of the solid layers. The first sub-boundary layers may be arranged in a third direction perpendicular to the top surface of the target layer. The second sub-boundary layers may be arranged in the third direction. Each of the second sub-boundary layers may lie between the first sub-boundary layers.

In some embodiments, the first and second sub-boundary layers may extend along a second direction that is parallel to the top surface of the target layer and crosses the first direction.

In some embodiments, the focusing structure may be obtained from a wing of a morpho butterfly.

In some embodiments, the apparatus may further comprise a controller that controls a distance between the light source and the focusing structure. The controller may places a top surface of the focusing structure in position within a Rayleigh range around a focal point of the laser.

In some embodiments, the apparatus may further comprise a matching structure between the focusing structure and the target layer. The matching structure may have a refractive index between those of the focusing structure and the target layer.

DETAILED DESCRIPTION OF EMBODIMENTS

Figure 1:
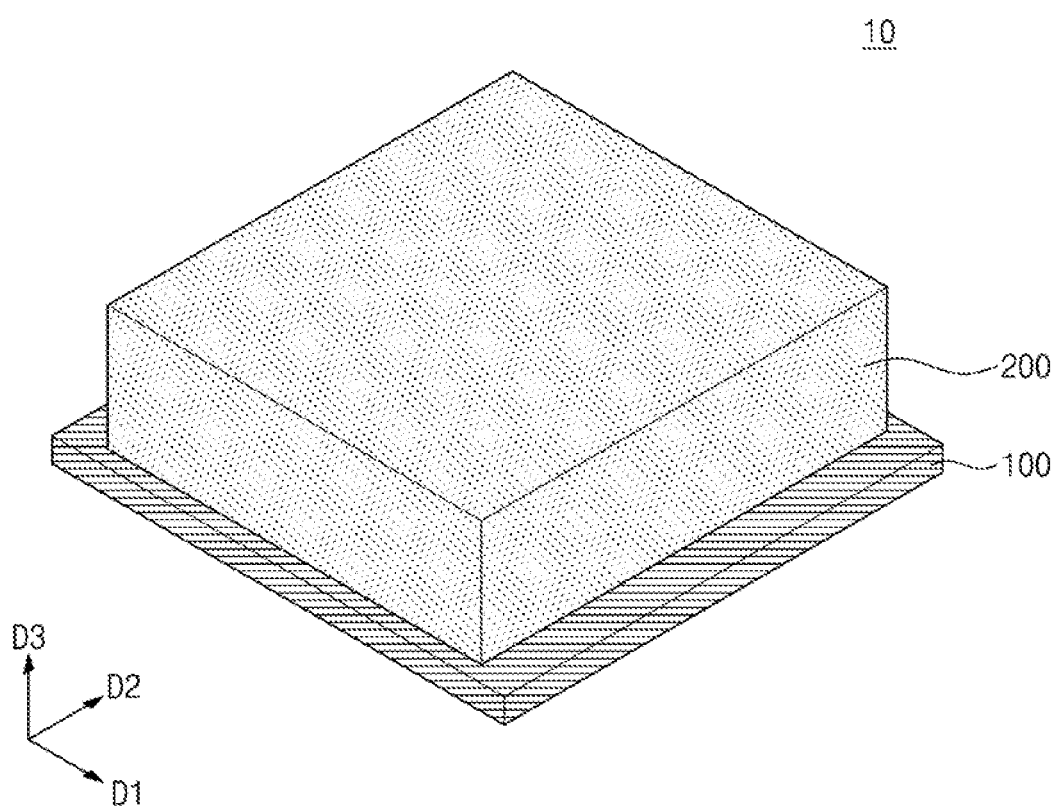
FIG. 1 illustrates a perspective view showing a target of an apparatus for generating charged particles according to exemplary embodiments of the present inventive concept.

In order to sufficiently understand the configuration and effect of the present invention, embodiments of the present invention will be described with reference to the accompanying drawings. It should be noted, however, that the present invention is not limited to the following exemplary embodiments, and may be implemented in various forms. Rather, the exemplary embodiments are provided only to disclose the present invention and let those skilled in the art fully know the scope of the present invention.

Like reference numerals refer to like elements throughout the specification. Embodiments described herein will be explained with reference to idealized exemplary views of the present technical inventive concept. In the drawings, thicknesses of layers and regions are exaggerated for effectively explaining the technical contents. Accordingly, regions exemplarily illustrated in the drawings have general properties, and shapes of regions exemplarily illustrated in the drawings are used to exemplarily disclose specific shapes but not limited to the scope of the present invention. Terms are used to describe various components in diverse embodiments of the present disclosure, but they should not limit the various components. These terms are only used to distinguish one element from another element. The exemplary embodiments explained and illustrated herein include complementary embodiments thereof.

The terminology used herein is for the purpose of describing particular embodiments only and is not intended to limit the present invention. As used herein, the singular forms are intended to include the plural forms as well. The terms 'comprises/includes' and/or 'comprising/including' used in the specification do not exclude the presence or addition of one or more other components.

It will be hereinafter described in detail exemplary embodiments of the present inventive concept with reference to the accompanying drawings.

FIG. 1 illustrates a perspective view showing a target of an apparatus for generating charged particles according to exemplary embodiments of the present inventive concept.

Referring to FIG. 1, an apparatus for generating charged particles may be provided with a target 10 including a target layer 100 and a focusing structure 200 on the target layer 100. In some embodiments, the target layer 100 may receive a laser to emit charged particles. For example, the charged particles may be cations and/or protons. For example, when the target layer 100 is a thin layer including carbon (C), carbon cations may be emitted from the target layer 100. It should be noted, however, that the emission of the charged particles from the target layer 100 is only exemplary. In other embodiments, the target layer 100 may emit a radiation (e.g., an X-ray).

The focusing structure 200 may be a porous layer. For example, the focusing structure 200 may include therein pores (not shown) and boundary layers (not shown) surrounding the pores. Exemplary structural features of the focusing structure 200 will be described below.

The focusing structure 200 may transform into a plasma layer (not shown) when being irradiated with laser (not shown). For example, on irradiation of laser, the focusing structure 200 may transform from a solid state into a gaseous state. The gaseous focusing structure 200 may receive energy from the irradiated laser and may then be ionized to transform into the plasma layer. The plasma layer may include therein free electrons and ions.

The free electrons of the plasma layer may be distributed to have a near-critical electron density based on a ratio of the boundary layers in the focusing structure 200. The near-critical electron density may mean an electron density whose value reaches the vicinity of a critical electron density. The critical electron density may refer to a free electron density at which the plasma frequency equals the frequency of an electromagnetic wave in plasma. For example, the near-critical electron density may be less than and about 0.7 times greater than the critical electron density. Alternatively, the near-critical electron density may be greater than and about 3 times less than the critical electron density. When the free electrons of the plasma layer have the near-critical electron density, a laser may be focused while passing through the plasma layer.

When the focusing structure 200 has an extremely high ratio of the boundary layers or is fully filled with the boundary layers, the free electrons of the plasma layer may have a density greater the near-critical electron density. When a laser is irradiated onto the plasma layer whose electron density is greater than the near-critical electron density, the laser may be reflected without passing through the plasma layer. The laser may thus not be focused.

When the focus structure 200 has an extremely low ratio of the boundary layers, the free electrons of the plasma layer may have a density less than the near-critical electron density. When a laser is irradiated onto the plasma layer whose electron density is less than the near-critical electron density, the laser may simply pass through the plasma layer. In this case, the laser may not be focused while passing through the plasma layer. The laser may thus not be focused.

The boundary layers may have a uniform distribution in the focusing structure 200. The free electrons may therefore have a uniform distribution in the plasma layer. The laser passing through the plasma layer may increase its focusing, or convergence, as the distribution uniformity of the free electrons grows. Accordingly, the focusing structure 200 of the present inventive concept may allow the laser to be maximally focused.

The charged particles emitted from the target layer 100 may have energy in proportion to laser intensity. In general, laser output is raised in order to increase laser intensity. However, high cost is required to raise the laser output.

According to the present inventive concept, a laser may be focused by the focusing structure 200 and then be provided to the target layer 100. Since laser intensity is in inverse proportion to an irradiation area of laser, when a laser is focused, the laser intensity may become increased. In this sense, charged particles (e.g., protons or cations) of high energy may be emitted from the target layer 100 receiving the focused laser.

Figure 2:
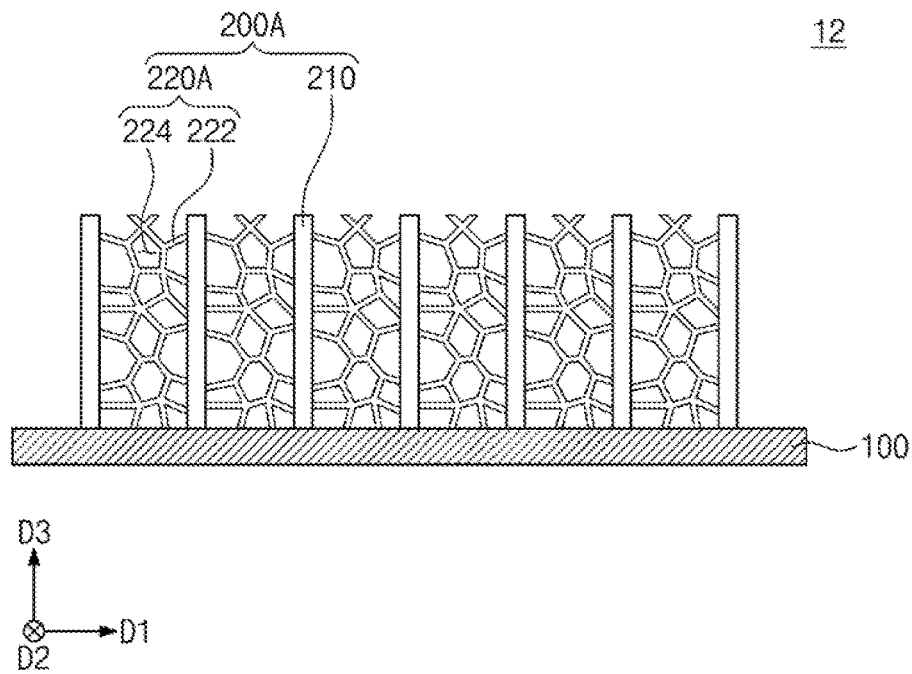
FIG. 2 illustrates a front view showing a target of an apparatus for generating charged particles according to exemplary embodiments of the present inventive concept.

FIG. 2 illustrates a front view showing a target of an apparatus for generating charged particles according to exemplary embodiments of the present inventive concept. Explanations substantially the same as those discussed with reference to FIG. 1 may be omitted for brevity of the description.

Referring to FIG. 2, an apparatus for generating charged particles may be provided with a target 12 including a target layer 100 and a first focusing structure 200A on the target layer 100. The target layer 100 may be configured substantially the same as that discussed with reference to FIG. 1. The first focusing structure 200A may correspond to the focusing structure 200 discussed with reference to FIG. 1.

The first focusing structure 200A may include solid layers 210 and first pore sections 220A alternately and repeatedly disposed along a first direction D1 parallel to a top surface of the target layer 100. The solid layers 210 may be arranged in the first direction D1. The solid layers 210 may include therein no cavities. For example, the solid layers 210 may be fully filled with their constituent material. The solid layers 210 may extend in a second direction D2 parallel to the top surface of the target layer 100 and crossing the first direction D1. Each of the solid layers 210 may have a constant width. The width may be a distance in the first direction D1 between opposite sidewalls of each solid layer 210. The present inventive concept, however, is not limited thereto. In other embodiments, each of the solid layers 210 may have opposite sidewalls at least one of which tapers as far away from the target layer 100. For example, each of the solid layers 210 may have a width that decreases with increasing distance from the target layer 100.

The first pore sections 220A may be arranged in the first direction D1. Each of the first pore sections 220A may be interposed between the solid layers 210. Each of the first pore sections 220A may include a porous layer. Each of the first pore sections 220A may include a boundary layer 222 and pores 224 surrounding the boundary layer 222. The boundary layer 222 may correspond to the boundary layer discussed with reference to FIG. 1. The boundary layer 222 may extend in an arbitrary direction. For example, the extending direction of the boundary layer 222 may not be specifically determined. As illustrated in FIG. 2, when the target 12 is viewed from its front side, the boundary layer 222 may have a mesh shape. It should be noted, however, that the shape of the boundary layer 222 of FIG. 2 is only exemplary. The boundary layer 222 may have a uniform distribution in each of the first pore sections 220A. For example, the boundary layer 222 may not be concentrated in a lower or upper portion of each first pore section 220A. The boundary layers 222 in the first pore sections 220A are illustrated to have the same shape, but it should be noted that the shape is only exemplary.

In some embodiments, the first focusing structure 200A may be obtained from natural substances. For example, the first focusing structure 200A may be obtained from wings of swallowtail butterflies. For example, cuticles of the wings of swallowtail butterflies may have a shape similar to that of the first focusing structure 200A. Accordingly, the cuticles may be detached from the wings of swallowtail butterflies and then be used as the first focusing structure 200A.

The first focusing structure 200A may transform into a plasma layer (not shown) when being irradiated with laser. The plasma layer may include free electrons having a near-critical electron density. The laser may thus be focused while passing through the plasma layer.

Since the boundary layers 222 have a uniform distribution in the first focusing structure 200A, the free electrons may also have a uniform distribution in the plasma layer. The laser may thus be maximally focused.

Figure 3:
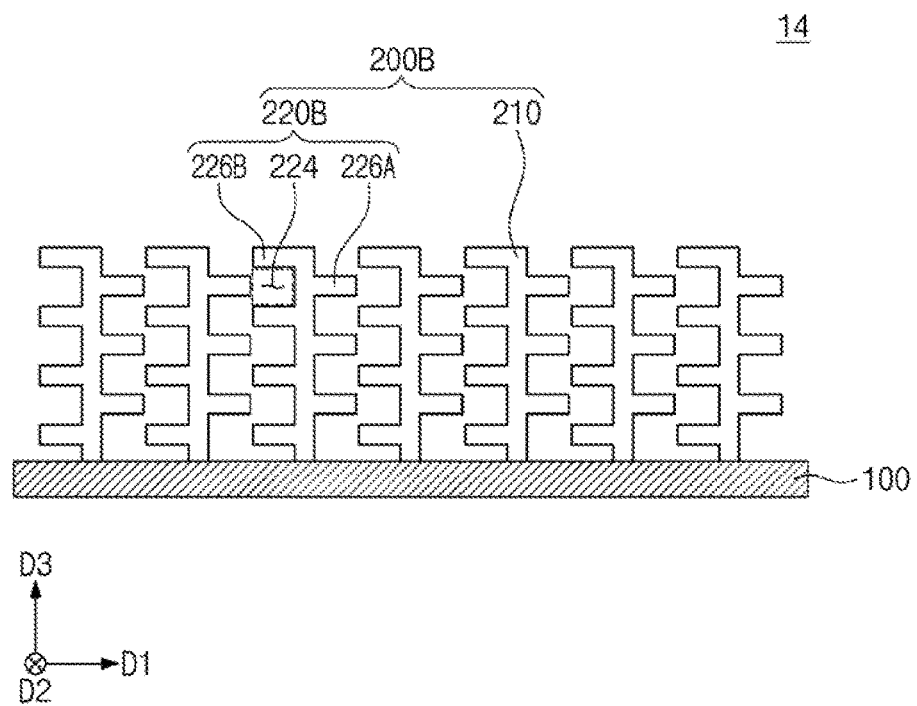
FIG. 3 illustrates a front view showing a target of an apparatus for generating charged particles according to exemplary embodiments of the present inventive concept.

FIG. 3 illustrates a front view showing a target of an apparatus for generating charged particles according to exemplary embodiments of the present inventive concept. Explanations substantially the same as those discussed with reference to FIGS. 1 and 2 may be omitted for brevity of the description.

Referring to FIG. 3, an apparatus for generating charged particles may be provided with a target 14 including a target layer 100 and a second focusing structure 200B on the target layer 100. The target layer 100 may be configured substantially the same as that discussed with reference to FIG. 2.

The second focusing structure 200B may include solid layers 210 and second pore sections 220B alternately and repeatedly disposed along a first direction D1. The solid layers 210 may be configured substantially the same as those discussed with reference to FIG. 2.

Each of the second pore sections 220B may include a porous layer. Each of the second pore sections 220B may include first sub-boundary layers 226A protruding in the first direction D1 from a sidewall of the solid layer 210. The first sub-boundary layers 226A are illustrated to have the same length along the first direction D1, but it should be noted that the same length is only exemplary. In other embodiments, the length of the first sub-boundary layer 226A may increase as approaching the target layer 100. The first sub-boundary layers 226A may be spaced apart from each other in a third direction D3 crossing a top surface of the target layer 100. For example, the first sub-boundary layers 226A may be arranged at a regular distance along the third direction D3. The first sub-boundary layers 226A may extend in a second direction D2.

Each of the second pore sections 220B may include second sub-boundary layers 226B protruding in a direction reverse to the first direction D1 from an opposing sidewall of the solid layer 210. The second sub-boundary layers 226B are illustrated to have the same length along the first direction D1, but it should be noted that the same length is only exemplary. In other embodiments, the length of the second sub-boundary layer 226B may increase as approaching the target layer 100. The second sub-boundary layers 226B may be spaced apart from each other in the third direction D3 crossing the top surface of the target layer 100. For example, the second sub-boundary layers 226B may be arranged at a regular distance along the third direction D3. The second sub-boundary layers 226B may extend in the second direction D2.

The first and second sub-boundary layers 226A and 226B may be arranged in a zigzag fashion along the third direction D3. For example, each of the second sub-boundary layers 226B may be placed between the first sub-boundary layers 226A directly adjacent to each other. The first and second sub-boundary layers 226A and 226B may not horizontally overlap each other. The present inventive concept, however, is not limited thereto. The first and second sub-boundary layers 226A and 226B may not vertically overlap each other. The present inventive concept, however, is not limited thereto. The numbers of the first and second sub-boundary layers 226A and 226B are exemplary illustrated in figures. The first and second sub-boundary layers 226A and 226B may have a uniform distribution in each of the second pore sections 220B. For example, the first and second sub-boundary layers 226A and 226B may not concentrate in a lower or upper portion of each second pore section 220B.

Pores 224 may be disposed between the first and second sub-boundary layers 226A and 226B. Shapes of the pores 224 may be determined by the first and second sub-boundary layers 226A and 226B and the solid layers 210.

In some embodiments, the second focusing structure 200B may be obtained from natural substances. For example, the second focusing structure 200B may be obtained from wings of morpho butterflies. For example, cuticles of the wings of morpho butterflies may have a shape similar to that of the second focusing structure 200B. Accordingly, the cuticles may be detached from the wings of morpho butterflies and then be used as the second focusing structure 200B.

The second focusing structure 200B may transform into a plasma layer (not shown) when being irradiated with laser. The plasma layer may include free electrons having a near-critical electron density. The laser may thus be focused while passing through the plasma layer.

Since the first and second sub-boundary layers 226A and 226B have a uniform distribution in the second focusing structure 200B, the free electrons may also have a uniform distribution in the plasma layer. The laser may thus be maximally focused.

Figure 4:
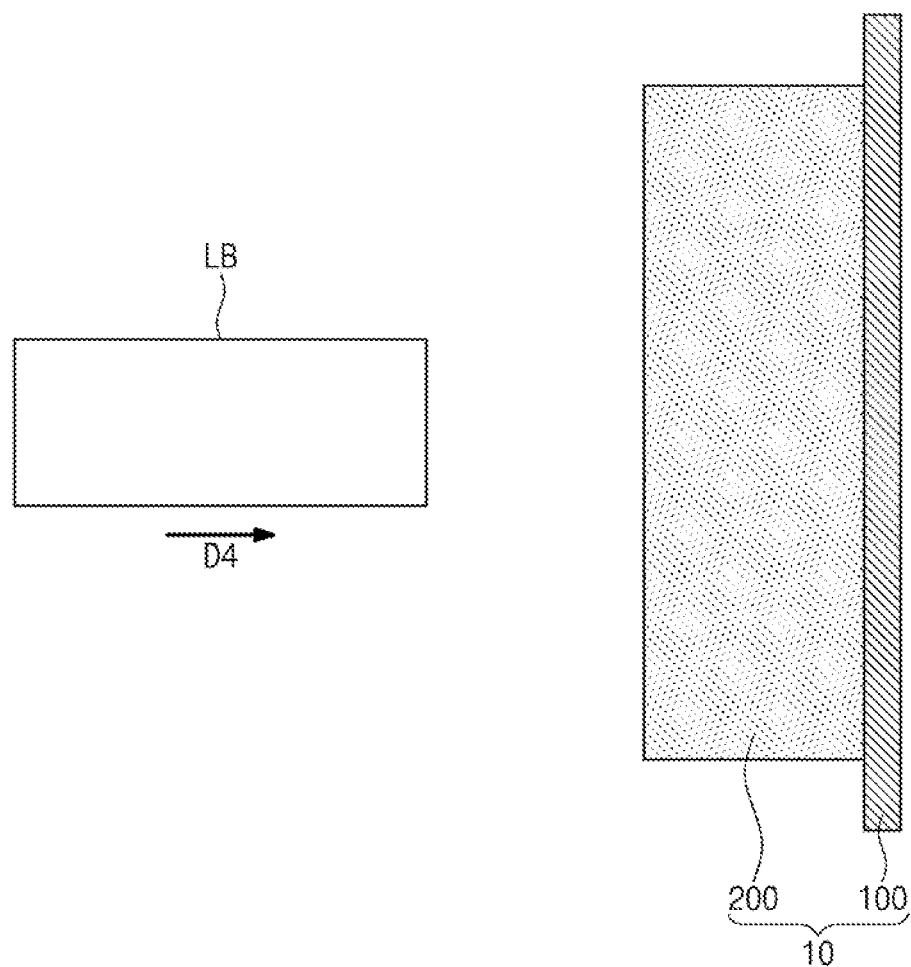
FIGS. 4 and 5 illustrate conceptual views showing a laser focusing according to exemplary embodiments of the present inventive concept.
Figure 5:
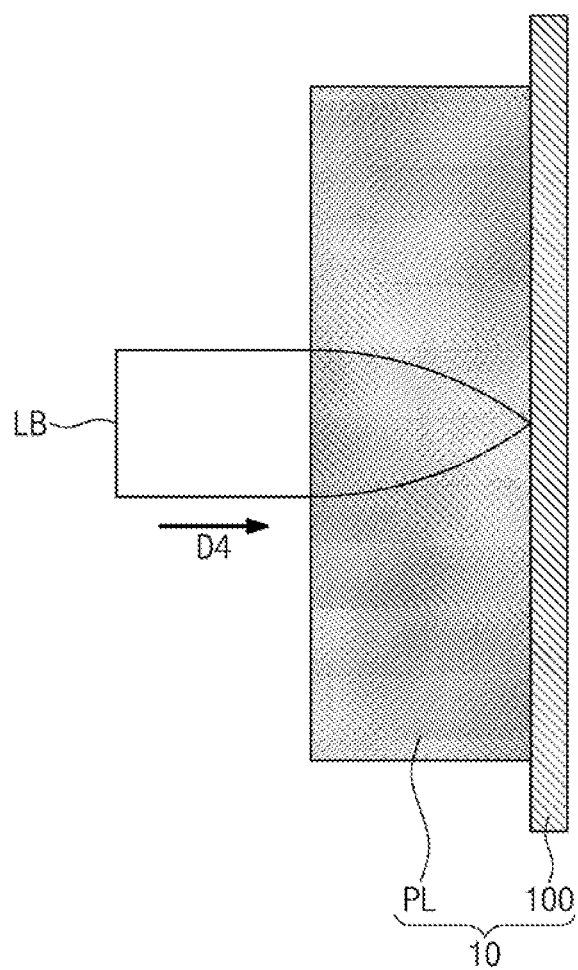

FIGS. 4 and 5 illustrate conceptual views showing a laser focusing according to exemplary embodiments of the present inventive concept. Explanations substantially the same as those discussed with reference to FIGS. 1 to 3 may be omitted for brevity of the description.

Referring to FIG. 4, a laser LB may travel in a fourth direction D4 toward a target 10 including a target layer 100 and a focusing structure 200. The target 10 may be substantially the same as the target 10 discussed with reference to FIGS. 1 to 3. The laser LB may travel toward a top surface of the target 10.

The laser LB may have a spatially Gaussian shape. For example, when the laser LB is viewed from its front side, the laser LB may have a Gaussian-shaped energy distribution in which energy decreases as away from a center of the laser LB.

Referring to FIG. 5, the laser LB may enter the target (see 10 of FIG. 4) to transform the focusing structure (see 200 of FIG. 4) into a plasma layer PL. The plasma layer PL may include ions (not shown) and free electrons (not shown). The free electrons may be distributed to have a near-critical electron density. The laser LB may pass through the plasma layer PL to interact with the free electrons, thereby causing self-focusing of the laser LB. The self-focusing may mean that the laser LB is automatically focused while passing through the plasma layer PL. The self-focusing is briefly explained below.

When the laser LB passes through the plasma layer PL, the free electrons may interact with the laser LB and may thus be pushed toward an outer portion of the laser LB. At this time, the free electrons may receive a pondermotive force produced from the interaction between the free electrons and the laser (LB). Accordingly, the free electrons may have a greater density at the outer portion of the laser LB than at a central portion of the laser LB. A phase velocity of the laser LB passing through the plasma layer PL may be relatively higher at a region where the density of the free electrons is high and relatively lower at a region where the density of the free electrons is low. Therefore, the phase velocity may be greater at the outer portion of the laser LB than at the central portion of the laser LB. As a result, the laser LB may be automatically focused, or self-focused.

Figure 6:
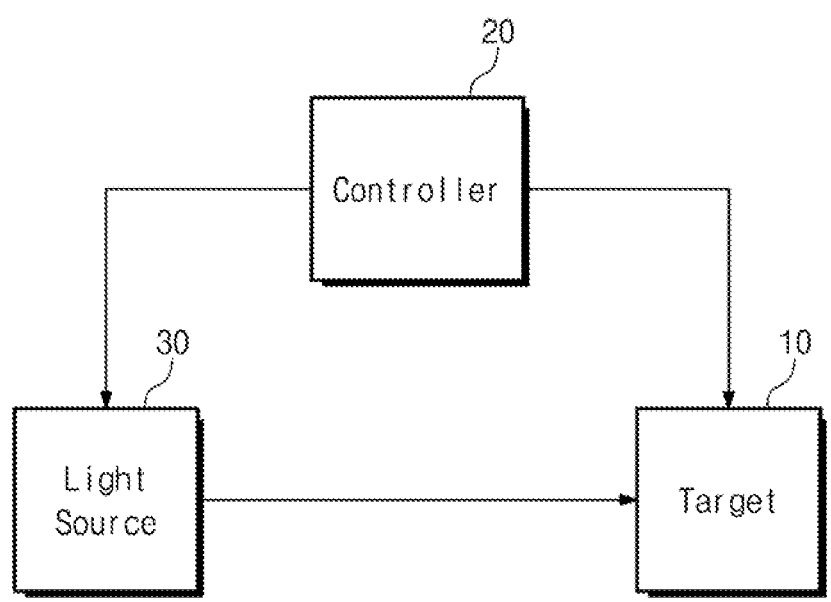
FIG. 6 illustrates a block diagram for explaining an apparatus for generating charged particles according to exemplary embodiments of the present inventive concept.
Figure 7:
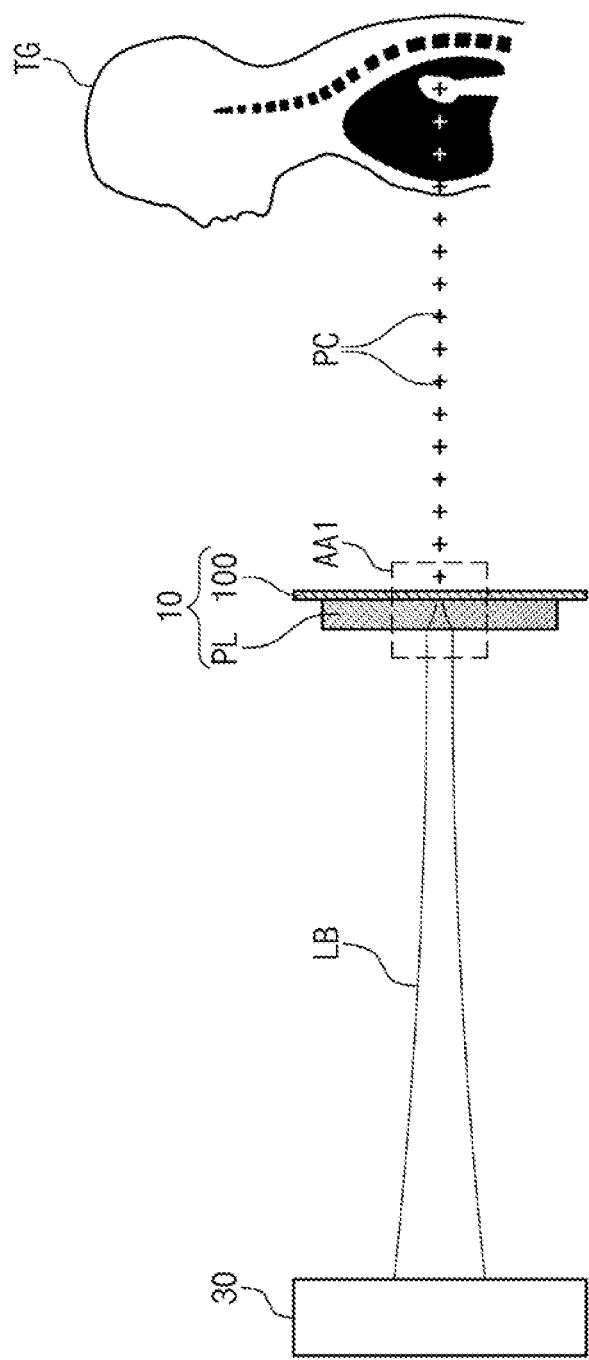
FIG. 7 illustrates a conceptual view showing an apparatus for generating charged particles according to exemplary embodiments of the present inventive concept.
Figure 8:
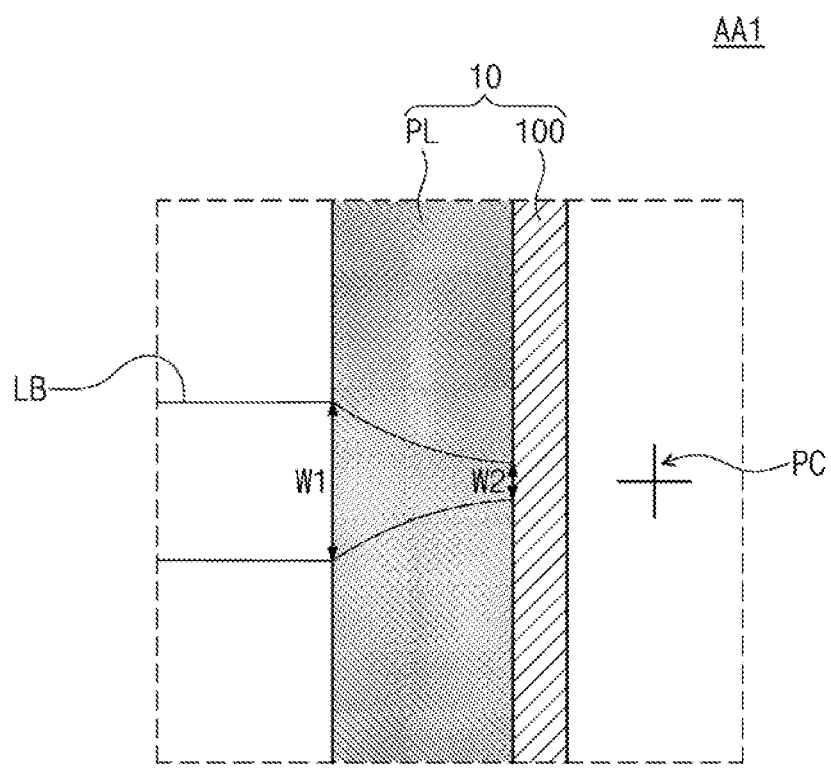
FIG. 8 illustrates an enlarged view of a portion AA1 of FIG. 7.

FIG. 6 illustrates a block diagram for explaining an apparatus for generating charged particles according to exemplary embodiments of the present inventive concept. FIG. 7 illustrates a conceptual view showing an apparatus for generating charged particles according to exemplary embodiments of the present inventive concept. FIG. 8 illustrates an enlarged view of a portion AA1 of FIG. 7. Explanations substantially the same as those discussed with reference to FIG. 1 may be omitted for brevity of the description.

Referring to FIGS. 6 to 8, an apparatus for generating charged particles may be provided to include a light source 30, a controller 20, and a target 10. The light source 30 may be controlled by the controller 20 and may emit a laser LB toward the target 10. For example, the light source 30 may emit a pulsed laser. The laser LB may have a Gaussian beam shape. For example, the laser LB may have a diameter, which is smallest at a focal point of the laser LB and increases as far away from the focal point of the laser LB.

The target 10 may be substantially the same as the target 10 discussed with reference to FIG. 1. As discussed with reference to FIGS. 4 and 5, the focusing structure 200 may focus the laser LB, and the focused laser LB may be provided to the target layer 100. For example, when the laser LB initially has a first diameter W1, after the laser LB is focused by the focusing structure 200, the first diameter W1 may be reduced to a second width W2 on a top surface of the target layer 100. Charged particles PC may be emitted from the target layer 100 that receives the laser LB having the second width W2. The charged particles PC may travel toward a target object TG. For example, the target object TG may be a human body.

In some embodiments, the controller 20 may control relative positions of the light source 30 and the target 10, so that a top surface of the focusing structure 200 may be placed within a Rayleigh range around the focal point of the laser LB. The present inventive concept, however, is not limited thereto.

According to the present inventive concept, the apparatus for generating charged particles may generate the charged particles PC having high energy by utilizing the focusing of the laser LB without raising laser output. Since the high-energy charged particles PC are generated without raising the laser output, the apparatus for generating charged particles may have improved efficiency in generating charged particles. Furthermore, since no additional devices are required to raise the laser output, costs for generating charged particles may be reduced or saved.

Figure 9:
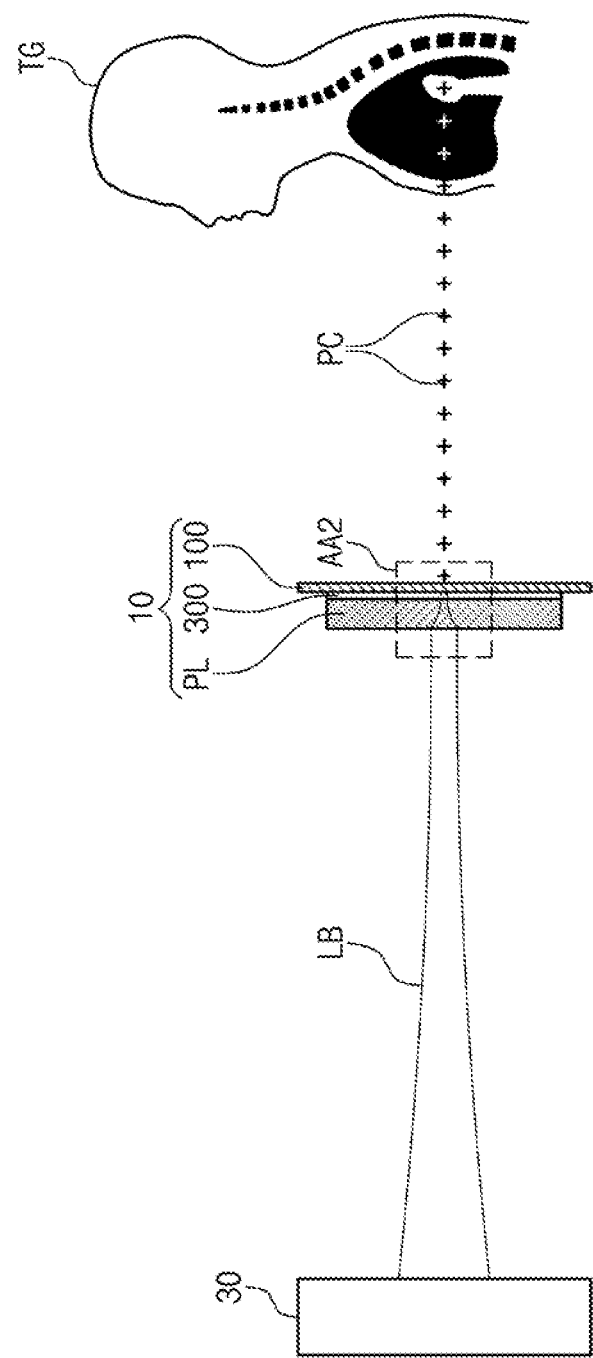
FIG. 9 illustrates a conceptual view showing an apparatus for generating charged particles according to exemplary embodiments of the present inventive concept.
Figure 10:
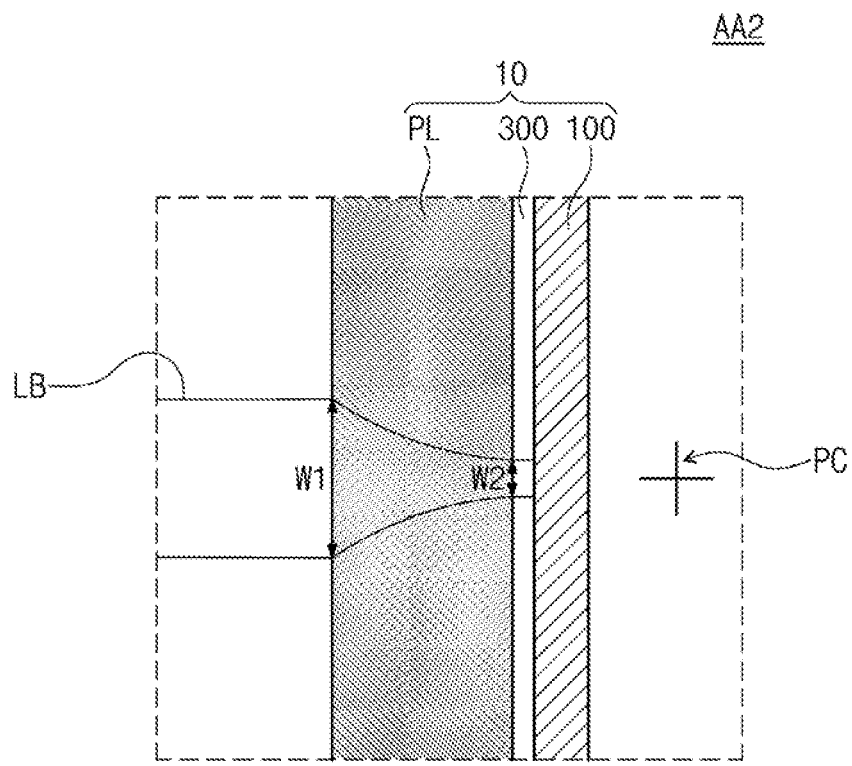
FIG. 10 illustrates an enlarged view of a portion AA2 of FIG. 9.

FIG. 9 illustrates a conceptual view showing an apparatus for generating charged particles according to exemplary embodiments of the present inventive concept. FIG. 10 illustrates an enlarged view of a portion AA2 of FIG. 9. Explanations substantially the same as those discussed with reference to FIGS. 6 to 8 may be omitted for brevity of the description.

Referring to FIGS. 9 and 10, a matching structure 300 may be provided between the focusing structure 200 and the target layer 100. The matching layer 300 may alleviate a difference in refractive index between the plasma layer PL and the target layer 100, and thereby the laser LB may decrease in energy loss occurring between the plasma layer PL and the target layer 100. For example, the matching structure 300 may have a refractive index between those of the plasma layer PL and the target layer 100.

According to the present inventive concept, since the laser LB is reduced in energy loss, efficiency may be improved in generating charged particles.

Furthermore, the efficiency in generating charged particles may also be maximized.

In addition, costs may be minimized in raising energy of charged particles.

However, the effect of the present inventive concept is not limited to the mentioned above.

The aforementioned description provides exemplary embodiments for explaining the present inventive concept. Therefore, the present inventive concept is not limited to the embodiments described above, and it will be understood by one of ordinary skill in the art that variations in form and detail may be made therein without departing from the spirit and essential features of the inventive concept.

What is claimed is:

1. An apparatus for generating charged particles, comprising:
   a light source that emits a laser;
   a target layer that receives the laser to generate charged particles; and
   a focusing structure that is between the light source and the target layer and focuses the laser,
   wherein the focusing structure comprises solid layers and pore sections alternately and repeatedly disposed along a first direction parallel to a top surface of the target layer, each of the pore sections comprising a porous layer.

2. The apparatus of claim 1, wherein the focusing structure transforms into a plasma layer when the laser is irradiated, wherein the plasma layer comprises free electrons that are distributed to have an electron density reaching a vicinity of a critical electron density of the plasma layer.

3. The apparatus of claim 2, wherein the electron density reaching the vicinity of the critical electron density is less than and 0.7 times greater than the critical electron density, or is greater than and 3 times less than the critical electron density.

4. The apparatus of claim 1, wherein each of the pore sections comprises pores and a boundary layer surrounding the pores.

5. The apparatus of claim 4, wherein the boundary layer has a uniform distribution in each of the pore sections.

6. The apparatus of claim 4, wherein the boundary layer has a mesh shape.

7. The apparatus of claim 6, wherein the focusing structure is obtained from a wing of a swallowtail butterfly.

8. The apparatus of claim 4, wherein the boundary layer comprises first sub-boundary layers and second sub-boundary layers protruding from a sidewall and an opposing sidewall, respectively, of each of the solid layers, the first sub-boundary layers being arranged in a third direction perpendicular to the top surface of the target layer, the second sub-boundary layers being arranged in the third direction, and each of the second sub-boundary layers being between the first sub-boundary layers.

9. The apparatus of claim 8, wherein the first and second sub-boundary layers extend along a second direction that is parallel to the top surface of the target layer and crosses the first direction.

10. The apparatus of claim 8, wherein the focusing structure is obtained from a wing of a morpho butterfly.

11. The apparatus of claim 1, further comprising a controller that controls a distance between the light source and the focusing structure, wherein the controller places a top surface of the focusing structure in position within a Rayleigh range around a focal point of the laser.

12. The apparatus of claim 1, further comprising a matching structure between the focusing structure and the target layer, wherein the matching structure has a refractive index between those of the focusing structure and the target layer.

* * * * *